(12) United States Patent
Hellenbrand (10) Patent No.: US 12,394,513 B2
(45) Date of Patent: *Aug. 19, 2025

(54) MEASURING AND VERIFYING DRUG PORTIONS

(71) Applicant: Becton Dickinson Rowa Germany GmbH, Kelberg (DE)

(72) Inventor: Christoph Hellenbrand, Kaifenheim (DE)

(73) Assignee: Becton Dickinson Rowa Germany GmbH, Kelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,744

(22) Filed: Apr. 10, 2023

(65) Prior Publication Data
US 2023/0245761 A1 Aug. 3, 2023

Related U.S. Application Data

(63) Continuation of application No. 17/520,381, filed on Nov. 5, 2021, now Pat. No. 11,664,117, which is a
(Continued)

(51) Int. Cl.
*G16H 30/40* (2018.01)
*G06T 7/00* (2017.01)
(Continued)

(52) U.S. Cl.
CPC ............. *G16H 30/40* (2018.01); *G06T 7/001* (2013.01); *G06T 7/80* (2017.01); *G06V 20/66* (2022.01); *G16H 20/13* (2018.01)

(58) Field of Classification Search
None
See application file for complete search history.

(56) References Cited

U.S. PATENT DOCUMENTS 7,028,723 B1 * 4/2006 Alouani ................. G16H 20/13
141/94
7,779,614 B1 8/2010 McGonagle
(Continued)

FOREIGN PATENT DOCUMENTS

CN 107531352 A 1/2018
KR 101744123 B1 6/2017
(Continued)

OTHER PUBLICATIONS

Anonymous: "Measuring Planar Objects with a Calibrated Camera—MATLAB & Simulink", Jan. 1, 2017, XP093007695, https://www.mathworks.com/help/releases/R2017b/vision/examples/measuring-planar-objects-with-a-calibrated-camera.html, 8 pages.
(Continued)

*Primary Examiner* — Dave Czekaj
*Assistant Examiner* — Shanika M Brumfield
(74) *Attorney, Agent, or Firm* — MASCHOFF BRENNAN (57) ABSTRACT

Methods for verifying drug portions include using a verification device to receive characteristic key data for a drug based on images of the drug and to receive, from the calibrated camera, a digital image of a package including a drug portion of the drug, the calibrated camera arranged to capture images from above the package, determine individual key data for the drug portion included in the package based at least on a known calibration parameter of the calibrated camera and the digital image of the package including the drug portion, compare the individual key data with the characteristic key data for the drug and verify or reject the package including the drug portion corresponding to the drug based on a result of the comparison. Systems and computer readable medium are also provided.

20 Claims, 4 Drawing Sheets

Related U.S. Application Data continuation of application No. 16/516,535, filed on Jul. 19, 2019, now Pat. No. 11,195,270.

(51) Int. Cl.
  *G06T 7/80* (2017.01)
  *G06V 20/66* (2022.01)
  *G16H 20/13* (2018.01)

(56) References Cited

U.S. PATENT DOCUMENTS

| | | | |
|---|---|---|---|
| 8,712,163 | B1 | 4/2014 | Osheroff |
| 9,262,585 | B2 * | 2/2016 | Keefe ............... G16H 70/40 |
| 10,456,915 | B1 | 10/2019 | Diankov |
| 10,565,735 | B2 | 2/2020 | Ghazizadeh |
| 2007/0211243 | A1 | 9/2007 | Laroche et al. |
| 2008/0056556 | A1 * | 3/2008 | Eller ............... G07F 17/0092 382/142 |
| 2008/0169044 | A1 * | 7/2008 | Osborne ............... B65B 3/003 141/1 |
| 2008/0306761 | A1 * | 12/2008 | George ............... G16H 20/10 705/2 |
| 2013/0088555 | A1 | 4/2013 | Hanina |
| 2013/0142406 | A1 | 6/2013 | Lang |
| 2013/0194414 | A1 | 8/2013 | Poirier |
| 2013/0343620 | A1 | 12/2013 | Okuda |
| 2014/0180476 | A1 | 6/2014 | Jaynes |
| 2014/0222444 | A1 | 8/2014 | Cerello |
| 2015/0066205 | A1 | 3/2015 | Braun |
| 2015/0169829 | A1 | 6/2015 | Jaynes |
| 2015/0302255 | A1 | 10/2015 | Gershtein et al. |
| 2016/0166766 | A1 | 6/2016 | Schuster |
| 2016/0203291 | A1 * | 7/2016 | Ebata ............... A61J 7/02 382/128 |
| 2016/0304229 | A1 | 10/2016 | Hellenbrand |
| 2017/0015445 | A1 | 1/2017 | Holmes |
| 2017/0065488 | A1 | 3/2017 | Thach |
| 2017/0264867 | A1 | 9/2017 | Amano et al. |
| 2018/0039731 | A1 | 2/2018 | Szeto |
| 2019/0244383 | A1 | 8/2019 | Glasner |
| 2019/0291277 | A1 | 9/2019 | Oleynik |
| 2019/0377977 | A1 | 12/2019 | Iwami |
| 2020/0082086 | A1 | 3/2020 | Nagaraju |
| 2020/0405578 | A1 | 12/2020 | Herman |
| 2021/0015711 | A1 | 1/2021 | Iwami |
| 2021/0313034 | A1 * | 10/2021 | Yokouchi ............... G16H 20/10 |

FOREIGN PATENT DOCUMENTS

| | | |
|---|---|---|
| WO | WO-0225568 A2 | 3/2002 |
| WO | WO-2013034504 A1 | 3/2013 |
| WO | WO-2014119994 A1 | 8/2014 |
| WO | WO-2015152225 A1 | 10/2015 |

OTHER PUBLICATIONS

European Office Action in Application No. 19187163.1 dated Dec. 19, 2022, 7 pages.
Extended European Search Report for Application No. 19187163.1, dated Jan. 23, 2020, 13 pages.
International Search Report and Written Opinion for Application No. PCT/EP2020/064802, dated Aug. 18, 2020, 21 pages.
Japanese Office Action for Application No. 2022-503519, dated Dec. 5, 2023, 12 pages including translation.
Chinese Office Action for Application No. 202080049550.6, dated Jun. 29, 2024, 14 pages including translation.
Japanese Office Action for Application No. 2022-503519, dated Jun. 4, 2024, 6 pages including translation.
Chinese Office Action for Application No. 202080049550.6, dated Nov. 29, 2024, 14 pages including machine translation.
European Office Action for Application No. 19187163.1, dated Sep. 11, 2024, 8 pages including translation.
Japanese Office Action for Application No. 2022-503519, dated Nov. 12, 2024, 8 pages including translation.
European Summons to attend oral proceedings for Application No. 19187163.1, dated Feb. 20, 2025, 23 pages including machine translation.

* cited by examiner

MEASURING AND VERIFYING DRUG PORTIONS

CROSS-REFERENCE TO RELATED APPLICATION

This application is a continuation application of U.S. patent application Ser. No. 17/520,381, filed on Nov. 5, 2021, which issued as U.S. Pat. No. 11,664,117 on May 30, 2023, entitled "MEASURING AND VERIFYING DRUG PORTIONS," which is a continuation application of U.S. patent application Ser. No. 16/516,535, entitled "MEASURING AND VERIFYING DRUG PORTION," filed Jul. 19, 2019, which issued as U.S. Pat. No. 11,195,270 on Dec. 7, 2021, the disclosure of each which is hereby incorporated by reference in its entirety.

BACKGROUND

The present disclosure relates to a method for measuring and verifying drug portions, a corresponding system comprising a measuring device, a storage device, and a verification device, and computer program products.

SUMMARY

One or more embodiments provide a method for verifying drug portions, comprising receiving, by a verification device, characteristic key data for a drug, the characteristic key data based on images for the drug; receiving a package including a drug portion of the drug, the package including an identifier for the drug portion included in the package; receiving, by the verification device, a digital image of the package from a calibrated camera arranged to capture images from above the package; determining, by the verification device, individual key data for the drug portion included in the package based at least on a known calibration parameter of the calibrated camera and the digital image of the package including the drug portion; comparing, by the verification device, the individual key data with the characteristic key data for the drug; and verifying or rejecting, by the verification device, the package including the drug portion corresponding to the drug based on a result of the comparing.

One or more embodiments provide a system for verifying for verifying drug portions, comprising: a calibrated camera; and a verification device in communication with the calibrated camera and a storage device, the verification device configured to: receive characteristic key data for a drug based on images of the drug; receive, from the calibrated camera, a digital image of a package including a drug portion of the drug, the calibrated camera arranged to capture images from above the package; determine individual key data for the drug portion included in the package based at least on a known calibration parameter of the calibrated camera and the digital image of the package including the drug portion; compare the individual key data with the characteristic key data for the drug; and verify or reject the package including the drug portion corresponding to the drug based on a result of the comparison.

One or more embodiments provide a non-transitory computer-readable medium comprising instructions stored therein, which when executed by one or more processors, cause the processors to: receive characteristic key data for a drug based on images of the drug; receive, from a calibrated camera, a digital image of a package including a drug portion of the drug, the calibrated camera arranged to capture images from above the package; determine individual key data for the drug portion included in the package based at least on a known calibration parameter of the calibrated camera and the digital image of the package including the drug portion; compare the individual key data with the characteristic key data for the drug; and verify or reject the package including the drug portion corresponding to the drug based on a result of the comparison.

The foregoing and other features, aspects and advantages of the disclosed embodiments will become more apparent from the following detailed description and accompanying drawings.

BRIEF DESCRIPTION OF THE DRAWINGS

The device according to the present disclosure and the method according to the present disclosure are described in greater detail below, with reference to the appended drawings.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Depending on the expansion stage, modern blister machines, as disclosed, for example, in WO 2013/034504 A1, which is incorporated by reference in its entirety, comprise several hundred supply and dispensing stations for drugs. A multiplicity of drug portions of a particular drug are stored in the supply and dispensing stations, respectively, and single or multiple drug portions can be dispensed upon request. With the blister machine, the drugs stored in the supply and dispensing stations are compiled and blistered patient-specifically according to the medically prescribed administration times.

For the compilation of the drug portions, corresponding supply and dispensing stations are actuated for dispensing one or more individual drug portions. When actuating a supply and dispensing station, a single drug portion is separated with a singulator and transferred via a dispensing opening of a guide device of the blister machine. By means of the guide device, a dispensed drug portion, optionally with the interposition of a collecting device, is fed to a packaging device which packages or blisters individual or multiple drug portions according to the medical requirements.

During the blistering by means of the packaging device, one or more drug portions is/are packaged in a blister bag which comprises patient-specific information as well as information about the drug portion(s) in the blister bag. For example, this information can be printed on a specific section of the blister bag. The blister bag itself is usually part of a blister tube which is guided out of the blister machine and stored for further processing. The further processing of the individual blister bags or of the blister tube regularly comprises a verification of the blister bags with regard to the drug portion or drug portions arranged in them in order to ensure that the drug portion(s), and only the drug portion or portions, which is/are supposed to be arranged in said blister bag, is/are arranged in a specific blister bag. In modern blister machines, the error rate with regard to the dispensing of a drug portion of a wrong drug type is very low. However, since the administration of a wrong drug type for a patient can have serious consequences, a follow-up inspection is an essential part of the blister bag production.

In order to detect incorrectly fitted blister bags, a blister tube can be guided through a control unit, with which a user verifies the accuracy of the filling of a blister bag, for example, in that an image of the blister bag to be verified is displayed on a screen and, using the display and a target composition also displayed on a screen, the user verifies whether the filling corresponds to the specification (i.e., the quantity of the present drug portions, whose appearance and possibly whose shape correspond to the specification of the target composition). With this process, it is also possible to detect if drug portions were broken by the singulation process and filled into the blister bag in a broken and damaged state.

The verification by a user is very time-consuming and costly. Therefore, automatic control units have been developed, with which a preliminary check is performed by machine, and a user is supposed to verify a blister bag only in case of inconclusive results of the mechanical verification. With the device disclosed in the aforementioned document, the quantity of drug portions arranged in a blister bag is determined by means of a camera and compared with the quantity which is supposed to be arranged according to a specification in the blister bag to be verified. However, with the control unit disclosed in said document, the drug portions are verified only in terms of their quantity. Incorrect drug portions cannot be recognized as long as their quantity corresponds to the specification.

With other known control units, parameters of the drug portions are determined using a camera image and an appropriate software. In order to identify individual drug portions, the parameters (or images or image sections) determined using the camera image are compared with stored target variables (or images).

A disadvantage of the aforementioned control units is that each system, prior to activation with the drug types it is supposed to verify, must be taught because the cameras of each inspection system are arranged slightly differently in each system, and due to deviations in the optics, they also produce slightly different images which deviate to different degrees from the appearances of the "real" drug portions (e.g., they recognize colors and shapes differently). Only by means of the teaching can it be ensured that, despite the abovementioned deviations, the control unit can correctly verify or recognize the drug portions.

It is the object of the present disclosure to provide a method and a system, with which a teaching of a device for verifying drug portions can be avoided.

According to one or more embodiments, this object is achieved by a method for measuring and verifying drug portions. The method may include, in a step a), characteristic key data of a drug type are initially compiled with a calibrated camera of a measuring device. Characteristic key data of a drug type are, for example, the size or shape of a drug portion, the color of the drug portion or its reflection pattern. Furthermore, it is possible to record as characteristic key data also the 3D profile of a drug portion of a drug type, which requires special cameras. Furthermore, the drug portion can be examined for damage, for example, using the 3D profile.

The characteristic key data are compiled by using the calibrated camera to generate at least one digital image of the drug portion and to transfer the generated digital image to a control unit. The control unit then uses the digital image to compile the characteristic key data for the drugs by means of an image processing program known from the prior art and taking into account the known calibration parameters of the camera.

As mentioned above, due to slight deviations in the camera optics, among others, and deviations with regard to the arrangement of the camera relative to the object to be imaged, each camera generates different digital images of the same object, and so image processing programs would compile deviating characteristic key data on the basis of the different digital images. It is therefore desired that a calibrated camera is used for generating the digital image of the drug portions, and so "normalized" characteristic key data are compiled with the measuring device. It is irrelevant which camera or which method is used to normalize the camera, as long as the characteristic key data reflect the true key data of the drug type (e.g., its correct size and color, and the like). Since certain deviations in shape, size and color occur during the production of the drug portions, it is customary to record a plurality of images, from which a plurality of key data are determined and from which a key data range is subsequently determined. However, within the scope of the application, this shall not be further mentioned explicitly, i.e., key data generally shall refer to key data ranges.

In a step b), the characteristic key data of the drug type are stored by the measuring device in a storage device. At least the aforementioned step a) is then repeated until the characteristic key data of all desired drug types have been obtained. It will be necessary to regularly determine new key data according to the above specification for new products or changes to the drug portions. These are then stored or updated in the storage device.

In order to be able to use the characteristic key data compiled by the measuring device for a verification, for example, of blistered drug portions, it is provided in a step c) that the characteristic key data are retrieved from or transmitted to a verification device.

The transmission to and from the storage device can be executed with any of the data transfer methods known from the prior art. For example, the storage device can possibly temporarily be connected to the control unit of the measuring device or verification device via a wireless or cable-based communication network. Alternatively, mobile data carriers, such as USB sticks or hard drives, can also be used for the "transferring."

In a step d), a calibrated camera of the verification device is used to compile individual key data for a drug portion to be verified and compare them with characteristic key data of the drug type, the presence of which is to be verified. In the following, reference shall be made to "one" drug portion. However, it is evident that a compilation of several drug portions can also be verified, and so in the following, the plural "drug portions" shall also be included.

The measuring device must be provided with information as to which drug portion(s) of which drug type(s) is/are to be verified. For example, this can be accomplished by acquiring data applied to a blister bag by means of a data detection unit, wherein the data contain information about the drug types included (e.g., indicate the target composition). As another example, the verification device can be provided with the data which were also provided to the blister machine for compiling the drug portions, and so the measuring device knows at all times which drug portion(s) of which drug type(s) is/are to be verified.

In order to be able to make a comparison between individual key data and characteristic key data, a calibrated camera of the verification device generates at least one digital image of a drug portion to be verified, transfers the generated digital image of the drug portion to be verified to a control unit, and the control unit determines individual key data for the drug portion to be verified using known calibration parameters of the camera, the verification device, and the digital image. If a compilation of multiple drug portions is to be verified, the individual key data can be generated on the basis of the camera and software used, using an image of all drug portions or multiple images (e.g., of one drug portion each). The individual key data are subsequently compared by a control unit with characteristic key data of the corresponding drug type(s), and based on the comparison results, the drug portion is verified or rejected. A drug portion is verified, when the characteristic key data coincide with the individual key data, while taking into account predetermined error margins.

Due to the use of a calibrated camera in both the measuring device and the verification device and the provision of the compiled characteristic key data to a storage device accessible to both the measuring device and the verification device, it is possible to provide a multiplicity of verification devices with the characteristic key data generated by a central measuring device without the need for the verification devices to be initially taught for all drug types that they are supposed to verify. The time-consuming, expensive and error-prone process of "teaching" a verification device is eliminated by accessing already existing characteristic key data, which requires that both the compilation of the characteristic key data of the drug types and the compilation of the individual key data of the drug portions are performed with calibrated cameras.

The aforementioned storage device can be part of a company-internal network, for example, and so the characteristic key data can be transmitted to all verification devices connected to the company network. In one or more embodiments, it is provided that the characteristic key data are stored via a network in a storage device, wherein the storage device is designed as a cloud storage on the Internet. By selecting a cloud storage as a storage location for characteristic key data, they can be made accessible at any time and worldwide to all users of verification devices, as long as the verification devices comprise appropriately calibrated cameras for capturing a digital image of the drug portion to be verified.

In order to ensure that the characteristic key data are only transmitted to or downloaded by those verification devices that are designed to be compatible (e.g., have a calibrated camera), it is provided in one or more embodiments that the verification device transmits an authentication code to the storage device, that the storage device verifies the authentication code, and that the characteristic key data can only be retrieved by or transmitted to the verification device if the authentication code is valid.

Due to changing manufacturing processes, the change, for example, of the shape of the drug portions of a drug type is a regular occurrence. In order to be certain at all times about the time that characteristic key data for a drug type were compiled, it is provided in one or more embodiments that during the compilation of the characteristic key data, they are provided with a time stamp that reflects the date of the compilation of the characteristic key data. If the characteristic key data comprise a time stamp, the verification device checks the time stamp of the characteristic key data associated with the individual key data prior to the comparison of the characteristic key data with the individual key data of the drug portion to be verified, and retrieves from the storage device and internally updates the characteristic key data, when a predetermined time difference is exceeded. In this manner, it can be avoided that characteristic key data that are too old are used for the comparison.

As already indicated above, it is possible that instead of a single drug portion, a compilation of drug portions, which can optionally comprise drug portions of different drug types, is to be verified. For example, it is conceivable that three or more drug portions of different drug types are present in a blister bag, the contents of which is to be verified. Here, a verification takes place in that individual key data of drug portions arranged, for example, in a blister bag are compiled by means of an image processing program and the calibration parameters and compared with the characteristic key data of the drug types that are supposed to be present in the blister bag. Due to the property of the characteristic key data, which characterize only the external appearance of a drug portion, it cannot be ruled out that drug portions of different drug types have identical characteristic key data. In order to avoid erroneous positive verifications during the verification of multiple drug portions of a compilation, it is provided in one or more embodiments that, during the verification of a compilation of multiple drug portions, the control unit of the verification device verifies the characteristic key data associated with the drug portions to be verified as to whether all drug portions of the compilation are clearly verifiable (e.g., it is verified whether possibly identical characteristic key data are present), in which case a clear verifiability is not given.

As already stated, it is important that the cameras of the measuring device and the verification device are calibrated, preferably by means of the same calibration method. For a calibration, both so-called "internal" camera parameters, which relate to the lens properties of the camera and the relative arrangement of lens and image sensor, for example, CCD or CMOS sensor, as well as so-called "external"

camera parameters, which relate to the geometric location, position, and orientation of the camera in space, and the lighting, must be determined. The calibration parameters result from the aforementioned parameters. For the calibration of a camera, any of a multiplicity of different calibration methods may be used.

In one or more embodiments, the calibration parameters KP(MESS), KP(VERI) of the cameras of the measuring and verification device are generated by creating digital images of a multiplicity of calibration objects with the cameras and comparing said images with key data for the calibration objects for generating the calibration parameters KP(MESS), KP(VERI).

In one or more embodiments, a system for measuring and verifying drug portions is provided. The system includes a measuring device, comprising means for compiling characteristic key data of a drug type by performing the step a) according to the aforementioned method, a storage device, comprising means for storing the characteristic key data by performing the step b) of the aforementioned method, and a verification device, comprising means for compiling individual key data for a drug portion to be verified and for comparing the individual key data with characteristic key data by performing steps c) and d) in accordance with the method according to the disclosure.

One or more embodiments provide a computer program product, comprising commands which prompt the measuring device of the system to compile and store in a storage device characteristic key data for a drug type by performing steps a) and b) in accordance with the methods described herein.

One or more embodiments provide a computer program product, comprising commands which prompt the verification device of the system to compile individual key data for drug portions to be verified and to compare them with characteristic key data by performing steps c) and d) in accordance with the method according to the disclosure.

Figure 1:
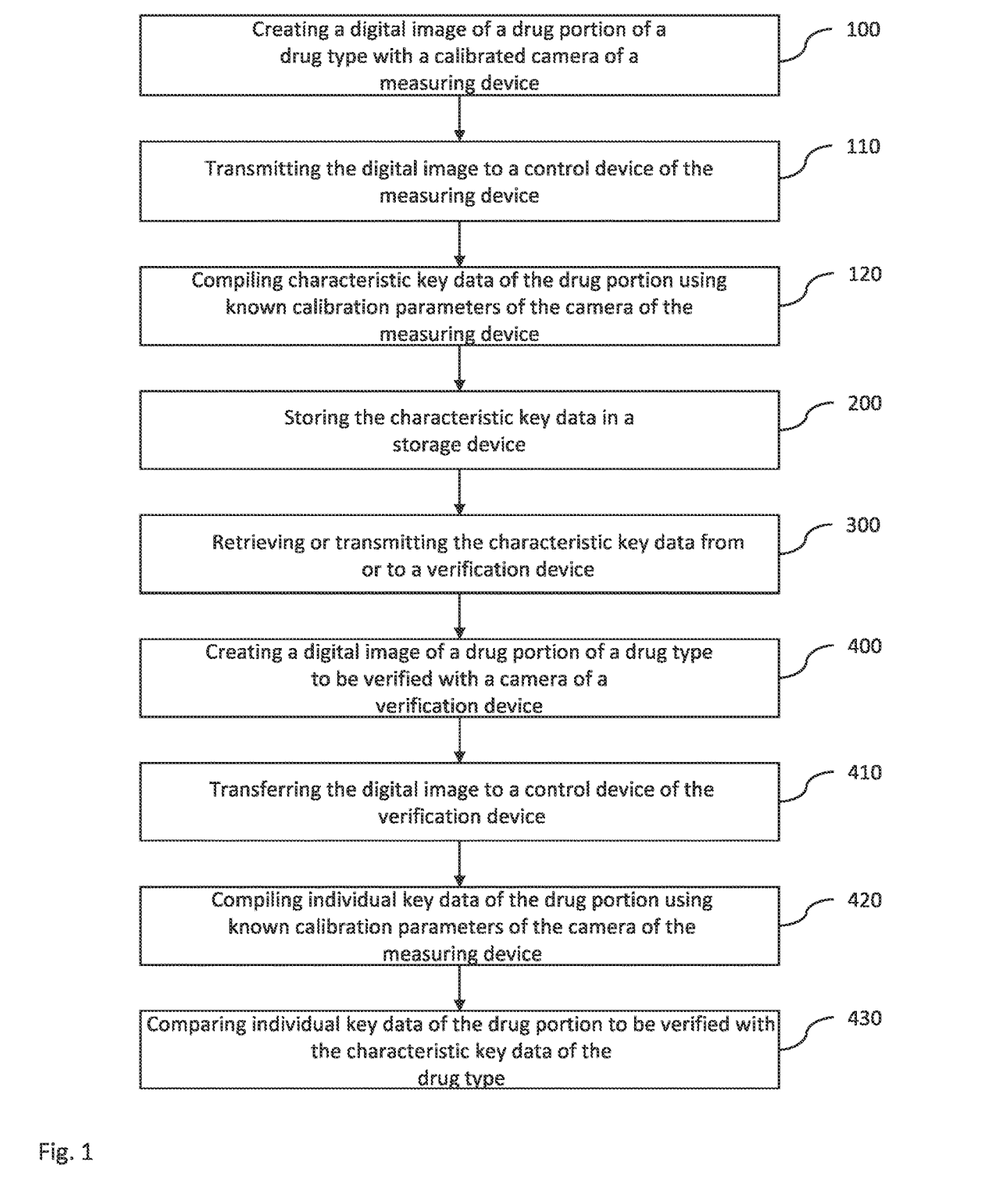
FIG. 1 is a flow chart of a method for measuring and verifying drug portions.

FIG. 1 shows a flow chart of a method for measuring and verifying drug portions. In a first step 100, a digital image of a drug portion of a drug type is compiled with a calibrated camera of a measuring device. As already mentioned above, in practice it is regularly the case that a multiplicity of images is produced, which are subjected to the following method steps, and so key data ranges are compiled instead of selective characteristic key data. In the following, this shall be assumed but not explicitly described further. In a step 110, the digital image is transmitted to a control unit of the measuring device. The control unit can be an integral component of the aforementioned camera, but it can also be designed as a conventional computer, for example, which can be controlled by a user via a screen. The transmission can be wireless or wire-based according to transmission methods known to a person skilled in the art. In a step 120, characteristic key data of the drug portion of a drug type are compiled using the digital image and taking into account known calibration parameters of the camera of the measuring device, wherein said key data can comprise, for example, size, shape, color of the drug portion. In accordance with the aforementioned method steps 100-120, characteristic key data are compiled for all drug types which are to be verified later.

In a step 200, the characteristic key data are stored in a storage device, which can take place at any time (e.g., the characteristic key data can be stored immediately after compilation or only after all drug types to be verified later have been processed). The type of storage device is not essential to the present disclosure. The transmission of the characteristic key data can be wire-based or wireless, but it is also conceivable to transfer the characteristic data to a mobile data carrier, such as a USB stick or a hard drive. In one or more embodiments, the storage device is designed as a cloud storage, which can be reached at any time worldwide, and so the characteristic key data are always and anywhere available to a third party.

In a step 300, the characteristic key data are retrieved from or transmitted to a verification device. This retrieval or transmission can also be wireless or wire-based. Again, it is conceivable that the storage device for a data transfer is temporarily connected to the verification device.

The following method steps are described with reference to a single drug portion, but also apply correspondingly to a compilation of multiple drug portions. In a step 400, a digital image is generated of a drug portion of a drug type to be verified with a calibrated camera of a verification device. In a step 410, the digital image is transmitted to a control unit of the verification device, wherein the description with regard to step 110 applies correspondingly. In a step 420, individual key data of the drug portion to be verified are compiled using an appropriately designed image processing software and the known calibration parameters of the camera of the verification device. In a step 430, the previously compiled individual key data of the drug portion to be verified are compared with the characteristic key data of the drug type that the verification device "expects," for example, in a blister bag (e.g., the drug type that was supposed to have been blistered by the blister machine according to the specification).

If the deviations between the individual key data and the characteristic key data do not exceed specific predetermined threshold values, the drug portion is positively verified (e.g., it is confirmed that the drug portion is a drug portion of the drug type that was expected by the verification device).

Figure 2:
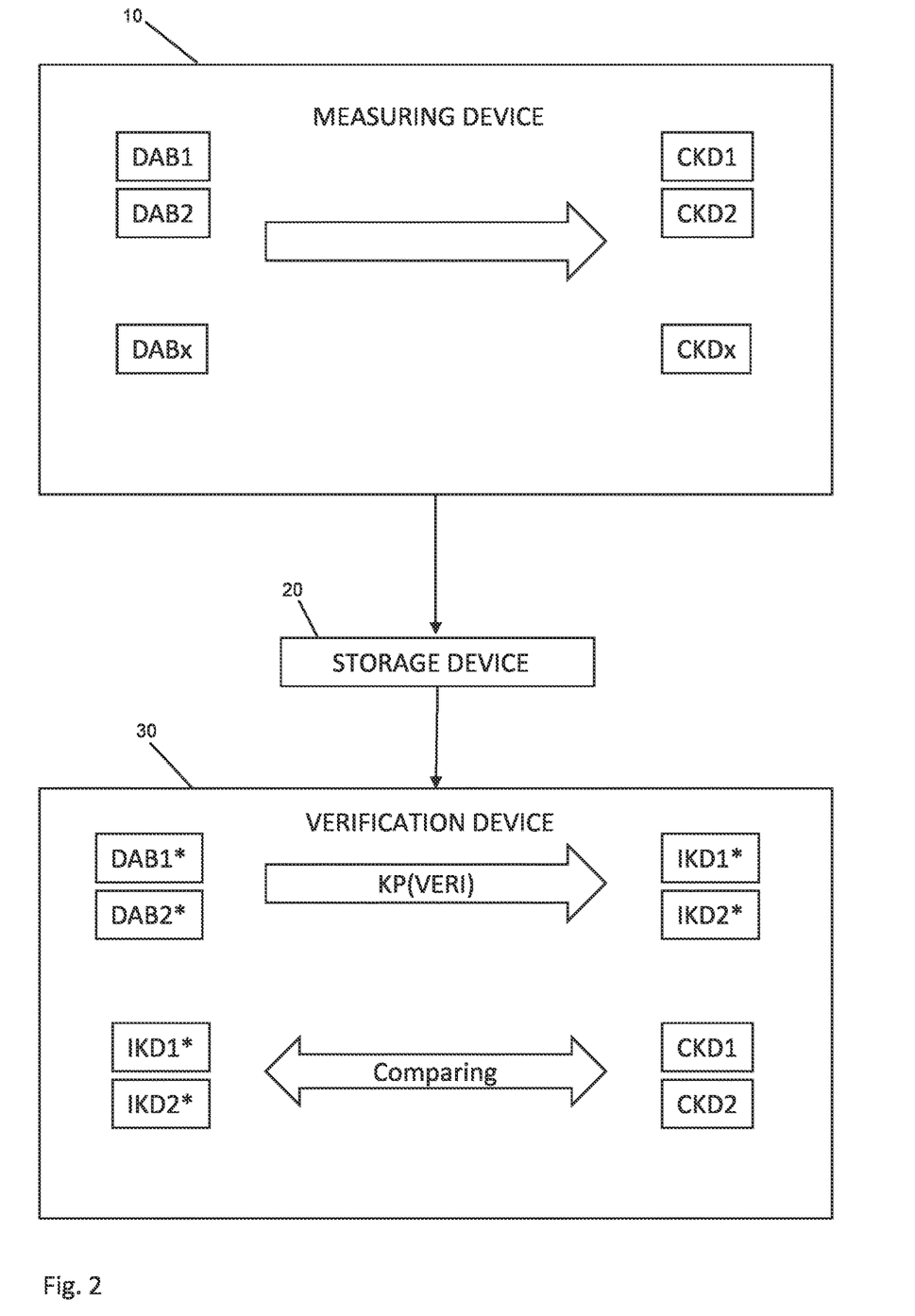
FIG. 2 is a schematic representation of a compilation of characteristic key data and a comparison with individual key data.

FIG. 2 shows schematically, how characteristic key data for a drug type are compiled, transmitted to a storage device, and compared with individual key data. The digital images DAB1-DABx are analyzed using an image processing software, and the characteristic key data CKD1-CKDx are compiled on the basis of the calibration parameters KP(MESS) of the camera of a measuring device 10. As already indicated above, the characteristic key data CKD1-CKDx are consistently a multiplicity of value ranges which reflect manufacturing tolerances in the production of the drug portions of the various drug types. The characteristic key data CKD1-CKDx are transmitted to a storage device 20, and transmitted from there to a verification device 30.

The verification device uses a calibrated camera to compile digital images DAB1* and DAB2* of drug portions to be verified. Using image processing software and methods, individual key data IKD1* and IKD2* are compiled for the drug portions to be verified, while taking into account the calibration parameters KP(VERI) of the camera of the verification device 30. These individual key data IKD1* and IKD2* are compared with the characteristic key data CKD1 and CKD2 of the drug types expected by the control unit of the verification device 30. The verification device 30 is notified in advance, which drug types or drug portions of the drug types are expected, for example, in that this information is read from a blister bag to be examined. Based on the comparison of the individual key data IKD1* and IKD2* with the characteristic key data CKD1 and CKD2, it is subsequently decided whether the drug portions correspond to the drug portions that were expected, while taking into account specific specifications.

Figure 3:
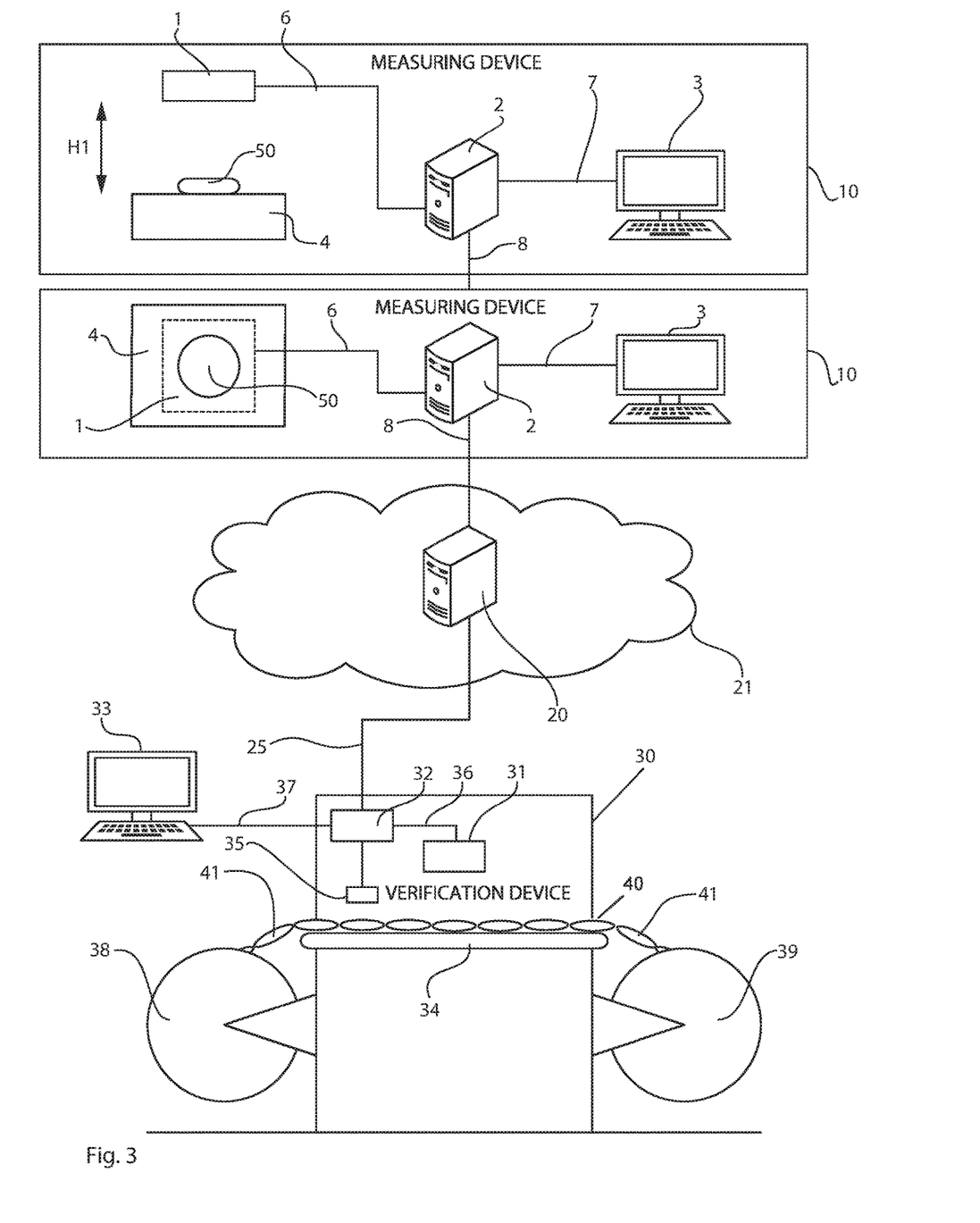
FIG. 3 is a schematic representation of a system for measuring and verifying drug portions.

FIG. 3 shows a schematic representation of a system for measuring and verifying drug portions. The upper section shows two views of the measuring device 10; a side view is shown in the upper section, and a top view is shown in the lower section, wherein only the "left" sections with the camera vary. The measuring device includes a camera 1, which is coupled via a line 6 to a control unit 2, which in turn is coupled via a line 7 to a display unit 3. Below the camera 1, a drug portion 50 of a drug type to be measured is arranged on a support table 4. The camera 1 has a predetermined distance H1 from the surface of the support table, wherein the distance H1 corresponds exactly to the distance that the camera 1 had to the support table 4 during the calibration of the camera 1 (e.g., a so-called external calibration parameter). In one or more embodiments, the control unit 2 is connected via a communication link 8 to a storage device 20, which in the embodiment shown is designed as a cloud storage which is part of the schematically indicated internet 21. Any wire-based and wireless transmission method(s) necessary for the transmission via the internet may be used.

The storage device 20 is connected via a communication link 25 to a control unit 32 of the verification device 30. The communication link 25 may be temporary, for example. The control unit 32 is connected via a line 37 to a display unit 33 and via a line 36 to a camera 31. In addition, the control unit 32 is coupled to a detection unit 35. In the embodiment shown, the camera 31 is arranged above a blister tube 40 consisting of multiple blister bags 41. The blister tube 40 is rolled around a roll 38 and is moved over a surface 34 and onto the roll 39 for verifying the drug portions in the individual blister bags 41. For this purpose, the roller 39 is driven by a motor (not depicted). With the camera 31, a digital image of the drug portion(s) in a blister bag 41 is generated and transmitted via the line 36 to the control unit 32. By means of the detection unit 35, data printed on the blister bags 41 are read out, the data indicating, among others, which drug portion(s) is/are supposed to be arranged in the individual blister bags 41.

The connection between any of the above described components may be wired or wireless. For example, any of lines 6, 7, 36, 37 or links 8, 25 may include wiring (e.g., Ethernet, RS232, twisted pair) or wireless connections (e.g., RF, Bluetooth).

Figure 4:
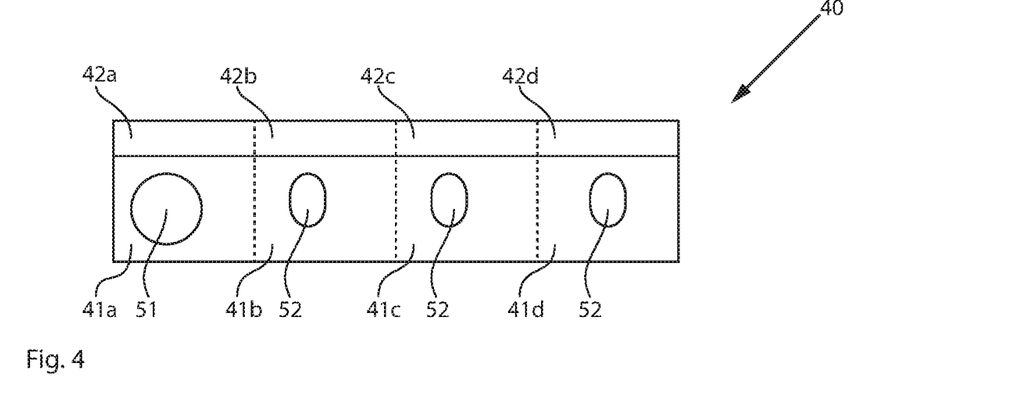
FIG. 4 is a top view of a blister tube with multiple blister bags.

FIG. 4 shows a schematic representation of a blister tube 40 with four blister bags 41a-41d and drug portions 51, 52 arranged in same. In the upper section, each blister bag 41a-41d includes a data section 42a-42d, in which information (not depicted) about the drug portions or types, which are supposed to be arranged in the blister bag 41a-41d, is printed.

Figure 5:
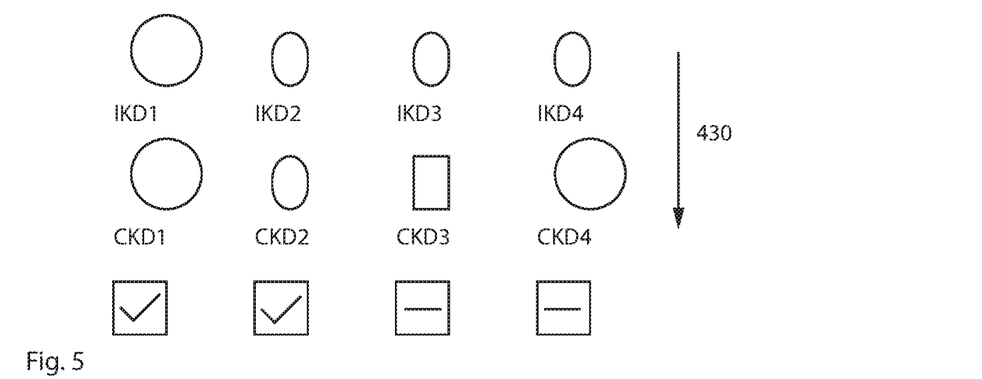
FIG. 5 is a schematic representation of a comparison and verification of individual key data and characteristic key data.

FIG. 5 illustrates schematically the verification of drug portions. In the upper row, individual key data IKD1-IKD4 relating to the shape of the drug portions are reproduced by visually depicting the shape of the drug portions located in the blister bags 41a-41d. The line below shows characteristic key data CKD1-CKD4 about the shape of those drug portions or types which are expected by the verification device in the blister bags 41a-41d. The bottom line according to FIG. 5 illustrates the result of the verification. The individual key data IKD1 and IKD2 are verified positively, and the individual key data IKD3 and IKD4 are verified negatively.

Figure 6:
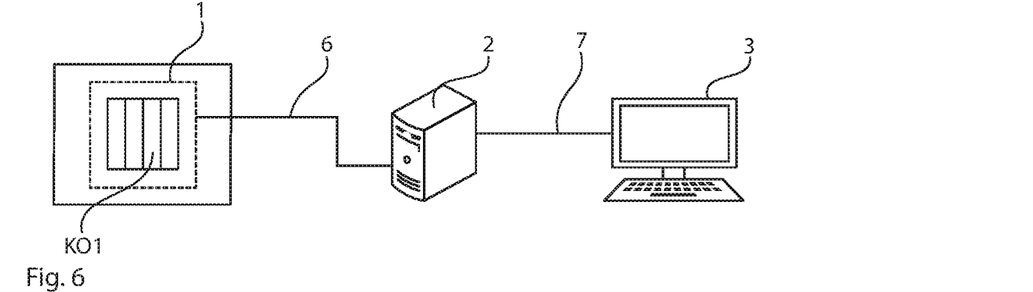
FIG. 6 is a schematic representation of a calibration process.

FIG. 6 roughly schematically illustrates, how the camera 1 of the measuring device is calibrated, wherein the same also applies to the camera 31 of a verification device. During calibration, a multiplicity of calibration objects, of which only one calibration object KO1 is shown, are placed under the camera 1, 31, and a digital image of the calibration objects is generated. Characteristic parameters for the measured calibration object KO1 are compiled by an image processing software, and using these characteristic parameters, it can be determined whether and to what extent the image produced by the camera 1, 31 deviates from the actual appearance of the calibration object KO1.

Figure 7:
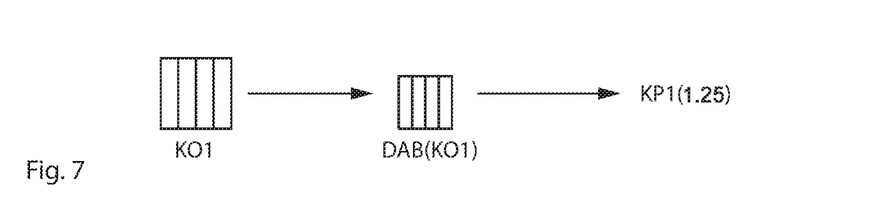
FIG. 7 is a schematic representation of a generation of a calibration parameter.

In FIG. 7, this is shown schematically for the characteristic parameter "size," wherein this representation is very simplified and supposed to merely show the principle. In the middle of FIG. 7, the results of the image processing for calibration object KO1 with respect to the parameter "size" are optically reproduced. Using the size differences, it is apparent that the size of the object according to the digital object does not correspond to the "true" size of the calibration object KO1. In the illustrated case, the size of the object DAB(KO1) according to the digital image is only 75%, though such a deviation does not typically occur in reality. Due to the described deviation, camera 1 has a calibration factor KP1 of 1.25 with respect to the characteristic parameter "size," i.e., the parameters determined with the image processing software must be converted with this calibration parameter in order to obtain the "true" characteristic parameter "size."

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject technology.

The word "exemplary" or the term "for example" is used herein to mean "serving as an example or illustration." Any aspect or design described herein as "exemplary" or "for example" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. A method for verifying drug portions, comprising:
receiving, by a first verification device and a second verification device, characteristic key data for a drug, the characteristic key data based on images for the drug captured by a calibrated measuring camera disposed over a support surface upon which the drug is arranged;
receiving a package including a drug portion of the drug, the package including an identifier for the drug portion included in the package;
receiving, by the first verification device and the second verification device, a digital image of the package from a calibrated verification camera arranged above the package and that is separate from the calibrated measuring camera;
determining, by each of the first verification device and the second verification device, individual key data for the drug portion included in the package based at least on a known calibration parameter of the calibrated verification camera and the digital image of the package including the drug portion;
comparing, by each of the first verification device and the second verification device, the individual key data with the characteristic key data for the drug; and
verifying or rejecting, by each of the first verification device and the second verification device, the package including the drug portion corresponding to the drug based on a result of the comparing.

2. The method of claim 1, further comprising:
retrieving the characteristic key data via a communication interface of a storage device attached to a wide area network.

3. The method of claim 1, further comprising:
transmitting, by one of the first verification device and the second verification device, an authentication code to retrieve the characteristic key data for the drug type;
verifying, by a storage device, the authentication code; and
retrieving, by the one of the first verification device and the second verification device, the characteristic key data from the storage device only if the authentication code is valid.

4. The method of claim 1, further comprising:
transmitting, by one of the first verification device and the second verification device, an authentication code to retrieve the characteristic key data for the drug type;
causing, by the one of the first verification device and the second verification device, verification of the authentication code by a storage device; and
causing, by the one of the first verification device and the second verification device, providing of the characteristic key data by the storage device to the one of the first verification device and the second verification device after determining the authentication code is valid.

5. The method of claim 1, further comprising, during compilation of the characteristic key data, providing a time stamp.

6. The method of claim 5, further comprising, prior to comparing the characteristic key data with the individual key data of the drug portion included in the package:

verifying, by one of the first verification device and the second verification device, the time stamp of the characteristic key data associated with the individual key data; and retrieving and updating, by the one of the first verification device and the second verification device, the characteristic key data from a storage device when a predetermined time difference is exceeded.

7. The method of claim 1, wherein the package includes multiple drug portions, and wherein said verifying or rejecting comprises:

verifying or rejecting the package, by one of the first verification device and the second verification device, based at least in part on the characteristic key data associated with respective drug types for each of the multiple drug portions and on the individual key data generated using a second image of the package.

8. The method of claim 1, further comprising:

obtaining, by an imaging device, a multiplicity of digital images of a calibration object having calibration characteristic data; and generating, by a controller of the imaging device, a calibration parameter for the imaging device based at least in part on key data for the calibration object and calibration data generated from the multiplicity of digital images, wherein the imaging device is one of the calibrated measuring camera or the calibrated verification camera, and wherein the controller is one of a measuring camera controller or a verification camera controller.

9. The method of claim 1, further comprising:

positively verifying, by one of the first verification device and the second verification device, the drug portion as being of the drug type if deviations from the comparing between the individual key data and the characteristic key data do not exceed specific predetermined threshold values.

10. The method of claim 1, further comprising:

wherein calibrating a camera comprises disposing the camera at a distance from a support table; and positioning the calibrated camera during use at the same distance from the support table as the camera was positioned during calibration.

11. The method of claim 1, wherein drug portions are disposed in one or more blister bags, wherein a plurality of blister bags are joined together in a blister tube, and the method further comprising:

moving the blister tube under the calibrated verification camera from a first roll to a second roll.

12. The method of claim 11, further comprising:

reproducing, by one of the first verification device and the second verification device, individual key data relating to a shape of the drug portions by visually depicting the shape of the drug portions located in the one or more blister bags.

13. A system for verifying drug portions, comprising:

a calibrated verification camera; and a plurality of verification devices in communication with the calibrated verification camera and a storage device, each of the plurality of verification devices configured to:

receive characteristic key data for a drug based on images of the drug captured by a calibrated measuring camera disposed over a support surface upon which the drug is arranged and that is separate from the calibrated verification camera;

receive, from the calibrated verification camera, a digital image of a package including a drug portion of the drug, the calibrated verification camera arranged above the package;

determine individual key data for the drug portion included in the package based at least on a known calibration parameter of the calibrated verification camera and the digital image of the package including the drug portion;

compare the individual key data with the characteristic key data for the drug; and verify or reject the package including the drug portion corresponding to the drug based on a result of the comparison.

14. The system of claim 13, wherein the packaged drug portion is enclosed within a blister bag included in a blister tube of joined blister bags, wherein the blister tube is arranged to pass within a field of view of the calibrated verification camera, wherein the system includes a first roll and a second roll, and wherein at least one of the first roll and the second roll rotate in response to the verification or rejection of the blister bag.

15. The system of claim 13, wherein a first verification device of the plurality of verification devices is configured to transmit an authentication code to retrieve the characteristic key data for the drug type; and wherein the first verification device is configured to cause the storage device to:

determine that the authentication code is valid; and after determining that the authentication code is valid, provide, to the first verification device, the characteristic key data.

16. The system of claim 13, wherein the calibrated verification camera is arranged above a surface supporting the packaged drug portion based on the known calibration parameter.

17. The system of claim 13, wherein the storage device is attached to a wide area network, and wherein the characteristic key data is retrieved from the storage device via a communication interface of the storage device.

18. The system of claim 13, wherein prior to comparing the individual key data with the characteristic key data for the drug, each of the plurality of verification devices is configured to:

verify a time stamp of the characteristic key data associated with the individual key data; and retrieve and update the characteristic key data when a predetermined time difference is exceeded.

19. A non-transitory computer-readable medium comprising instructions stored therein, which when executed by one or more processors of a plurality of verification devices, cause the processors of each of the plurality of verification devices to:

receive characteristic key data for a drug based on images of the drug captured by a calibrated measuring camera disposed over a support surface upon which the drug is arranged;

receive, from a calibrated verification camera that is separate from the calibrated measuring camera, a digital image of a package including a drug portion of the drug, the calibrated verification camera arranged to capture images from above the package;

determine individual key data for the drug portion included in the package based at least on a known calibration parameter of the calibrated verification camera and the digital image of the package including the drug portion;

compare the individual key data with the characteristic key data for the drug; and verify or reject the package including the drug portion corresponding to the drug based on a result of the comparison.

20. The non-transitory computer-readable medium of claim 19, wherein the characteristic key data comprises a range for a characteristic of the drug type, wherein the instructions stored therein, which when executed by the one or more processors, cause the processors to generate the range based on a plurality of digital images of the drug type and the calibration parameter.

* * * * *